United States Patent [19]  
Hirschmann

[11] 4,156,010  
[45] May 22, 1979

[54] (R)-(−)-3-{[2-(P-HYDROXYPHENYL)-1-METHYLETHYL]-AMINOMETHYL}-3,4-DIHYDRO-2H-1,5-BENZODIOXEPIN-3-OL

[75] Inventor: Ralph F. Hirschmann, Blue Bell, Pa.

[73] Assignee: Merck & Co., Inc., Rahway, N.J.

[21] Appl. No.: 864,171

[22] Filed: Dec. 27, 1977

[51] Int. Cl.² .................. A61K 31/335; C07D 319/08; A61K 31/74
[52] U.S. Cl. ................................ 424/278; 260/340.3; 424/78; 424/80; 424/81
[58] Field of Search ....................... 260/340.3; 424/278

[56] References Cited  
U.S. PATENT DOCUMENTS 3,700,691  10/1972  Wasson et al. ..................... 260/340.3

Primary Examiner—Ethel G. Love  
Attorney, Agent, or Firm—Edmunde D. Riedl; Mario A. Monaco

[57] ABSTRACT

The isomer (R)-(−)-3-{[2-(p-hydroxyphenyl)-1-methylethyl]-aminomethyl}-3,4-dihydro-2H-1,5-benzodioxepin-3-ol and its non-toxic acid addition salts is unexpectedly more potent in the reduction of elevated interocular pressure in mammals than its enantiomorph or the racemate thereof.

11 Claims, No Drawings

(R)-(−)-3-{[2-(P-HYDROXYPHENYL)-1-METHYLETHYL]-AMINOMETHYL}-3,4-DIHYDRO-2H-1,5-BENZODIOXEPIN-3-OL

DISCLOSURE OF THE INVENTION

Pharmaceuticals such as pilocarpine are presently used for the treatment of glaucoma. Although useful, they generally exhibit side effects such as extreme miosis, spasm of accomodation, night blindness and transient blurred vision. In mammals, the isomer (R)-(−)-3-{[2-(p-hydroxyphenyl)-1-methylethyl]-aminomethyl}-3,4-dihydro-2H-1,5-benzodioxepin-3-ol is effective in reducing intraocular pressure both in normal and hypertensive eyes, while at the same time eliminating or substantially reducing the side effects associated with pilocarpine medication.

The present invention therefore relates to a method of treating glaucoma and ocular hypertension by applying an effective amount of (R)-(−)-3-{[2-(p-hydroxyphenyl)-1-methylethyl]-aminomethyl}-3,4-dihydro-2H-1,5-benzodioxepin-3-ol or a non-toxic ophthalmologically acceptable salt thereof to the hypertensive mammalian eye. The invention also relates to a method of reducing normal intraocular pressure. The invention further relates to ophthalmic compositions comprising this compound. In particular this invention relates to the discovery that an individual isomer of 3-{[2-(p-hydroxyphenyl)-1-methylethyl]-aminomethyl}-3,4-dihydro-2H-1,5-benzodioxepin-3-ol is unexpectedly more potent than either the racemate or its enantiomorph as an agent for reducing intraocular pressure which partially or totally eliminates one or more of the above-mentioned side effects.

The racemate of the base compound is disclosed in U.S. Pat. No. 3,700,691 as a useful β-adrenergic stimulating agent uniquely suitable as a bronchodilating agent. That racemate has the structure:

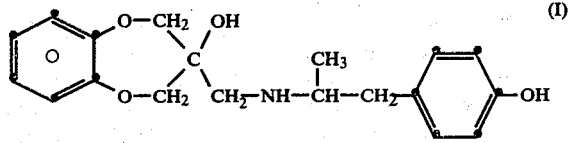

The isomer having the configuration (R)-(−)-3-[2-(p-hydroxyphenyl)-1-methylethyl]-aminomethyl-3,4-dihydro-2H-1,5-benzodioxepin-3-ol and the perspective structural formula:

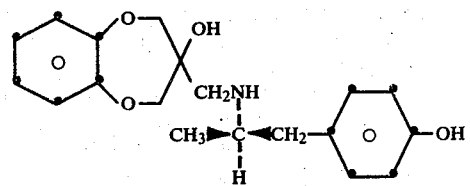

as shall be demonstrated is now found to show a remarkably unexpected and surprising difference in activity as shall hereinafter be demonstrated. The racemate (I) of compound II is known to be useful as a β-adrenergic blocking agent as is described in U.S. Pat. No. 3,700,691.

The resolution of 1-methyl-2-(4-hydroxyphenyl)-ethylamine is described at page 528 of J. van Dijk et al, Recueil, 84:521 (April, 1965). Thus, several recrystallizations of racemic 1-methyl-2-(4-hydroxyphenyl)-ethylammonium hydrogen D(−)-tartrate from water afford R-(−)-1-methyl-2-(4-hydroxyphenyl)-ethylammonium hydrogen D-(−)-tartrate, m.p. 202°–203.5° dec., $[\alpha]_D = 31.6°$ (C=4.0, water); while the L(+)-tartaric acid salt of the racemic base gives (+)-1-methyl-2-(4-hydroxyphenyl)-ethylammonium hydrogen L(+)-tartrate, m.p. 203°–204° dec., $[\alpha]_D = +31.25°$ (C=4.0, water).

Conversion of these tartrates to the bases give R-(−)-1-methyl-2-(4-hydroxyphenyl)-ethylamine, m.p. 108.5°–110° (from toluene), $[\alpha]_D - 35.5°$ (C=2.0, ethanol) and S(+)-1-methyl-2-(4-hydroxyphenyl)-ethylamine, m.p. 110°–111° (from toluene), $[\alpha]_D + 37.1°$ (C=2.0, ethanol). At least an equimolar amount of 3,4-dihydro-2H-1,5-benzodioxepin-3-spiro oxirane is then admixed with R-(−)-1-methyl-2-(4-hydroxyphenyl)-ethylamine in a suitable solvent for the amine such as a loweralkanol. The solvent must, of course, be inert to reactants and products in the sense that the solvent does not irreversibly react with either reactants or products so as to hinder the course of the intended reaction. The reaction is allowed to proceed preferably at ambient temperature, e.g., about 20° C., for a period of from 12–120 hours. The reaction is more rapid at higher temperatures (up to 30° C.), but the yields can be anticipated to be lessened because of by-product formation.

The product II can be then purified by any suitable means, although recrystallization from $C_1$–$C_8$ alkanol is preferred. The recrystallization can be repeated until a material of desired purity is obtained.

In a preferred embodiment, the R-(−)-3-{[2-(p-hydroxyphenyl)-1-methylethyl]-aminomethyl}-3,4-dihydro-2H-1,5-benzodioxepin-3-ol is then prepared as follows. A suspension of 3,4-dihydro-2H-1,5-benzodioxepin-3-spirooxirane (712 mg., 4 mmole) in a solution of R-(−)-1-methyl-2-(4-hydroxyphenyl)-ethylamine (604 mg., 4 mmole) in methanol (8 ml.) is stirred at room temperature for five days. The solution is evaporated to dryness and the residual oil is dissolved in isopropanol (8 ml.). The isopropanol solution is diluted with water to the point of turbidity and the product allowed to crystallize for 24 hours. The solid (1.09 g., m.p. 113°–115°) is dissolved in hot isopropanol (5½ parts volume by weight) and the filtered solution is allowed to stand for five hours at room temperature and then overnight at ca. 5° R-(−)-3-{[2-(p-hydroxyphenyl)-1-methylethyl]-aminomethyl}-3,4-dihydro-2H-1,5-benzodioxepin-3-ol is obtained by crystallization in the form of very small needles, m.p. 113°–114°, $[\alpha]_D = -33.1°$ (C=2.0, ethanol).

Analysis $C_{19}H_{23}NO_4$ requires: C, 69.28; H, 7.04; N, 4.25. Found: C, 68.94; H, 7.36; N, 4.32.

In a similar way S(+)-1-methyl-2-(4-hydroxyphenyl)-ethylamine was converted to the R(+)-benzodioxepin derivative, m.p. 113°–114°.

When the two optical isomers of compound I, that is compound II and its enantiomorph as the dihydrogen phosphate salts are tested for their ocular hypotensive effects and cardiac side effects after topical administration to the rabbit eye, the following results are obtained. In normotensive animals, compound II is more potent in reducing the intraocular pressure (IOP) than its enantiomorph especially at low concentrations such as 0.05%. In the water loading test, the two isomers antagonized the elevation of IOP in a dose related manner. Compound II was 50 times more potent than its enantiomorph (ED 50=0.001% and 0.05% respectively). In rabbits with alpha chymotrypsin-induced glaucoma, compound II is the more potent compound when the first four hours after installations are taken into account. Thereafter, the two isomers are equally effective. As with other beta-adrenergic stimulants, the two isomers produced increases in heart rate. A significant tachycardia is induced by a 0.005% concentration of compound II and a 0.5% concentration of its enantiomorph. However, with compound II, the tachycardia occurred with doses 100 times higher than that required to decrease the IOP. Compound II is not found to modify the pupil diameter or cause eye irritation.

The compound of this invention is preferably administered in the form of ophthalmic pharmaceutical compositions adapted for topical administration to the eye such as solutions, ointments or as a solid insert. Formulations of this compound may contain from 0.01 to 5% and especially 0.5 to 2% of medicament. Higher dosages as, for example, about 10% or lower dosages can be employed provided the dose is effective in lowering intraocular pressure. As a unit dosage form between 0.001 to 5.0 mg., preferably 0.005 to 2.0 mg., and especially 0.005 to 1.0 mg. of the compound is generally applied to the human eye, generally on a daily basis.

The pharmaceutical preparation which contains the compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidine, isopropyl myristate and other conventionally employed acceptable carriers. The pharmaceutical preparation may also contain non-toxic auxiliary substances such as emulsifying, preserving, wetting, bodying agents and the like, as for example, polyethylene glycols 200, 300, 400 and 600, carbowaxes 1,000, 1,500, 4,000, 6,000 and 10,000, bacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid and the like.

Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The pharmaceutical preparation may also be in the form of a solid insert. For example, one may use a solid water soluble polymer as the carrier for the medicament. The polymer used to form the insert may be any water soluble non-toxic polymer, for example, cellulose derivatives such as methylcellulose, sodium carboxymethyl cellulose, hydroxyloweralkyl cellulose, hydroxyethyl cellulose, hydroxypropyl cellulose, hydroxypropylmethyl cellulose; acrylates such as polyacrylic acid salts, ethylacrylates, polyacrylamides; natural products such as gelatin, alginates, pectins, tragacanth, karaya, chondrus, agar, acacia; the starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum and mixtures of said polymer.

If a solid insert is employed, it preferably is prepared from cellulose derivatives such as methyl cellulose, hydroxyethyl cellulose, hydroxypropyl cellulose or hydroxypropylmethyl cellulose or from other synthetic materials such as polyvinyl alcohol, polyvinyl pyrrolidone, polyethylene oxide or polyvinyl methylether.

Hydroxypropyl cellulose, one of the preferred polymers for the preparation of the insert is available in several polymeric forms, all of which are suitable in the preparation of these inserts. Thus, the product sold by Hercules, Inc. of Wilmington, Del. under the name KLUCEL such as KLUCEL HF, HWF, MF, GF, JF, LF and EF which are intended for food or pharmaceutical use are particularly useful. The molecular weight of these polymers useful for the purposes described herein may be at least 30,000 to about 1,000,000 or more.

Similarly, an ethylene oxide polymer having a molecular weight of up to 5,000,000 or greater, and preferably 100,000 to 5,000,000 can be employed.

Further, for example, POLYOX a polymer supplied by Union Carbide Co. may be used having a molecular weight of about 50,000 to 5,000,000 or more and preferably 3,000,000 to 4,000,000. Other specific polymers which are useful are polyvinyl pyrrolidine having a molecular weight of from about 10,000 to about 1,000,000 or more, preferably up to about 350,000 and especially about 20,000 to 60,000; polyvinyl alcohol having a molecular weight of from about 30,000 to 1,000,000 or more, particularly about 400,000 and especially from about 100,000 to about 200,000; hydroxypropylmethyl cellulose having a molecular weight of from about 10,000 to 1,000,000 or more, particularly up to about 200,000 and especially about 80,000 to about 125,000; methyl cellulose having a molecular weight of from about 10,000 to about 1,000,000 or more, preferably up to about 200,000 and especially about 50 to 100,000; and CARBOPOL (carboxyvinyl polymer) of B. F. Goodrich and Co. designated as grades 934, 940 and 941.

For the purpose of this invention the type and molecular weight of the polymer is not critical. Any water soluble polymers can be used having an average molecular weight which will afford dissolution of the polymer and accordingly the medicament in any desired length of time. The inserts, therefore, can be prepared to allow for retention and accordingly effectiveness in the eye for any desired period. The insert can be in the form of a square, rectangle, oval, circle, doughnut, semi-circle, ¼ moon shape, and the like. Preferably, the insert is in the form of a rod, doughnut, oval or ¼ moon. The insert can be readily prepared, for example, by dissolving the medicament and the polymer in a suitable solvent and the solution evaporated to afford a thin film of the polymer which can then be subdivided to prepare inserts of appropriate size. Alternatively, the insert can be prepared by warming the polymer and the medicament and the resulting mixture molded to form a thin film. Preferably, the inserts are prepared to molding or extrusion procedures well known in the art. The molded or extruded product can then be subdivided to afford inserts of suitable size for administration in the eye.

The insert can be of any suitable size to readily fit into the eye. For example, castings or compression molded films having a thickness of about 0.25 mm. to 15.0 mm. can be subdivided to obtain suitable inserts. Rectangular segments of the cast or compressed film having a thickness between about 0.5 and 1.5 mm. can be cut to afford shapes such as rectangular plates of 4×5–20 mm. or ovals of comparable size. Similarly, extruded rods having a diameter between about 0.5 and 1.5 mm. can be cut into suitable sections to provide the desired amount of polymer. For example, rods of 1.0 to 1.5 mm. in diameter and about 20 mm. long are found to be satisfactory. The inserts may also be directly formed by injection molding. It is preferred that the ophthalmic inserts containing the medicament of the present invention be formed so that they are smooth and do not have any sharp edges or corners which could cause damage to the eye. Since the term smooth and sharp edges or corners are subjective terms, in this application these terms are used to indicate that excessive irritation of the eye will not result from the use of the insert.

The ocular medicinal inserts can also contain plasticizers, buffering agents and preservatives. Plasticizers suitable for this purpose must, of course, also be completely soluble in the lacrimal fluids of the eye. Examples of suitable plasticizers that might be mentioned are water, polyethylene glycol, propylene glycol, glycerine, trimethylol propane, di- and tripropylene glycol, hydroxypropyl sucrose and the like. Typically, such plasticizers can be present in the ophthalmic insert in an amount ranging from up to 1 to about 30% by weight. A particularly preferred plasticizer is water which is present in amounts of at least about 5% up to about 40%. In actual practice, a water content of from about 10% to about 20% is preferred since it may be easily accomplished and adds the desired softness and pliability to the insert.

When plasticizing the solid medicinal product with water, the product is contacted with air having a relative humidity of at least 40% until said product picks up at least about 5% water and becomes softer and more pliable. In a preferred embodiment, the relative humidity of the air is from about 60% to about 99% and the contacting is continued until the water is present in the product in amounts of from about 10% to about 20%.

Suitable water soluble preservatives which may be employed in the insert are sodium bisulfate, sodium thiosulfate, ascorbate, benzalkonium chloride, chlorobutanol, thimerosal, phenylmercuric acetate, phenylmercuric borate, parabens, benzyl alcohol and phenyl ethanol. These agents may be present in amounts of from 0.001 to 5% by weight of solid insert, and preferably 0.1 to 2%.

Suitable water soluble buffering agents are alkali, alkali earth carbonates, phosphates, bicarbonates, citrates, borates, and the like, such as sodium phosphate, citrate, borate, acetate, bicarbonate and carbonate. These agents may be present in amounts sufficient to obtain a pH of the system of between 5.5 to 8.1 and especially 7–8; usually up to about 2% by weight of polymer. The insert may contain from about 1 mg. to 100 mg. of water soluble polymer, more particularly from 5 to 50 mg. and especially from 5 to 20 mg. The medicament is present from about 0.1 to about 25% by weight of insert.

The following examples serve to more fully illustrate this invention.

EXAMPLE 1

Solution Composition

| | | |
|---|---|---|
| (R)-(−)-3-{[2-(p-hydroxyphenyl)-1-methylethyl]aminomethyl}-3,4-dihydro-2H-1,5-benzodioxepin-3-ol hydrogen phosphate | 1 mg. | 15 mg. |
| Sodium phosphate monobasic . 2H$_2$O | 9.38 mg. | 6.10 mg. |
| Dibasic sodium phosphate . 12H$_2$O | 28.48 mg. | 16.80 mg. |
| Benzalkonium chloride | 0.10 mg. | 0.10 mg. |
| Sodium hydroxide q.s. | pH 6.8 | pH 6.8 |
| Water for injection q.s. ad. | 1.0 ml. | 1.0 ml. |

(R)-(−)-3-{[2-(p-hydroxyphenyl)-1-methylethyl]aminomethyl}-3,4-dihydro-2H-1,5-benzodioxepin-3-ol, phosphate buffer salts, and benzalkonium chloride are added to and dissolved in water. The pH of the solution is adjusted to 6.8 with sodium hydroxide and the final solution diluted to volume. The solution is rendered sterile by filtration through a sterilizing filter.

EXAMPLE 2

| | |
|---|---|
| (R)-(−)-3-{[2-(p-hydroxphenyl)-1-methylethyl]aminomethyl}-3,4-dihydro-2H-1,5-benzodioxepin-3-ol hydrogen phosphate | 5 mg. |
| Petrolatum q.s. ad. | 1 gram |

(R)-(−)-3-{[2-(p-hydroxyphenyl)-1-methylethyl]aminomethyl}-3,4-dihydro-2H-1,5-benzodioxepin-3-ol and the petrolatum are aseptically combined.

EXAMPLE 3

| | |
|---|---|
| (R)-(−)-{[2-(p-hydroxphenyl)-1-methylethyl]aminomethyl}-3,4-dihydro-2H-1,5-benzodioxepin-3-ol hydrogen phosphate | 1 mg. |
| Hydroxypropylcellulose q.s. | 12 mg. |

Ophthalmic inserts are manufactured from compression molded films prepared on a Carver Press by subjecting the powder mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrated insert are then autoclaved at 250° F. for ½ hour.

EXAMPLE 4

| | |
|---|---|
| (R)-(−)-3-{[2-(p-hydroxphenyl)-1-methylethyl]aminomethyl}-3,4-dihydro-2H-1,5-benzodioxepin-3-ol hydrogen phosphate | 1 mg. |
| Hydroxypropyl cellulose q.s. ad. | 12 mg. |

Ophthalmic inserts are manufactured from a solvent cast film prepared by making a viscous solution of the powder using methanol as the solvent. The solution is placed on a polytetrafluoroethylene plate and allowed to dry at ambient conditions. After drying, the film is placed in an 88% relative humidity cabinet until it is pliable. Appropriately sized inserts are cut from the film.

EXAMPLE 5

| | |
|---|---|
| (R)-(—)-{[2-(p-hydroxphenyl)-1-methylethyl]aminomethyl}-3,4-dihydro-2H-1,5-benzodioxepin-3-ol hydrogen phosphate | 1 mg. |
| Hydroxypropyl methyl cellulose q.s. ad. | 12 mg. |

Ophthalmic inserts are manufactured from a solvent cast film prepared by making a viscous solution of the powder blend using a methanol/water solvent system (10 ml. methanol is added to 2.5 g. of powder blend, to which 11 ml. of water (in three divided portions) is added). The solution is placed on a Teflon polytetrafluoroethylene plate and allowed to dry at ambient conditions. After drying, the film is placed in an 88% R.H. cabinet until it is pliable. Appropriately sized inserts are then cut from the film.

EXAMPLE 6

| | |
|---|---|
| (R)-(—)-{[2-(p-hydroxphenyl)-1-methylethyl]aminomethyl}-3,4-dihydro-2H-1,5-benzodioxepin-3-ol hydrogen phosphate | 1 mg. |
| Hydroxypropyl methyl cellulose q.s. ad. | 12 mg. |

Ophthalmic inserts are manufactured from compression molded films which are prepared on a Carver Press by subjecting the powder mixture of the above ingredients to a compressional force of 12,000 lbs. (gauge) at 350° F. for one minute. The film is cooled under pressure by having cold water circulate in the platen. Ophthalmic inserts are then individually cut from the film with a punch. Each insert is placed into a vial, which is then placed in a humidity cabinet (88% R.H. at 30° C.) for two to four days. After removal from the humidity cabinet, the vials are stoppered and then capped. The vials containing the hydrated insert are then autoclaved at 250° F. for one-half hour.

Acid addition salts other than the dihydrogen phosphate can be employed so long as they are non-toxic and non-irritating to the eye. Some examples of pharmaceutically acceptable anions are set forth at page 2 of Journal of Pharm. Sciences, 66(1), Jan., 1977. These are easily obtained by neutralization of the base compound with an equivalent amount of the appropriate acid.

What is claimed is:

1. A method of treating glaucoma and of lowering intraocular pressure which comprises topically applying to the eye an intraocular pressure lowering effective amount of (R)-(—)-3-{[2-(p-hydroxyphenyl)-1-methylethyl]aminomethyl}-3,4-dihydro-2H-1,5-benzodioxepin-3-ol or a non-toxic acid addition salt thereof which is free from (S)-(+)-3-{[2-(p-hydroxyphenyl)-1-methylethyl]aminomethyl}-3,4-dihydro-2H-1,5-benzodioxepin-3-ol.

2. A method according to claim 1 wherein the acid addition salt is the hydrogen maleate salt.

3. A method according to claim 1 wherein the acid addition salt is the dihydrogen phosphate salt.

4. An ophthalmic composition for the lowering of intraocular pressure comprising an intraocular pressure reducing amount of (R)-(—)-3-{[2-(p-hydroxyphenyl)1-methylethyl]aminomethyl}-3,4-dihydro-2H-1,5-benzodioxepin-3-ol or an acid addition salt thereof and an ophthalmic carrier, which composition is free from (S)-(+)-3-{[2-(p-hydroxyphenyl)-1-methylethyl]aminomethyl}-3,4-dihydro-2H-1,5-benzodioxepin-3-ol.

5. A composition according to claim 4 wherein the acid addition salt is the hydrogen maleate salt.

6. A composition according to claim 4 wherein the acid addition salt is the dihydrogen phosphate salt.

7. The composition of claim 4 wherein the carrier is a solid water soluble polymer.

8. The composition of claim 4 wherein the carrier is hydroxypropyl cellulose.

9. An ophthalmologically acceptable water soluble polymeric insert comprising an intraocular pressure lowering effective amount of (R)-(—)-3-[2-p-hydroxyphenyl)-1-methylethyl]aminomethyl-3,4-dihydro-2H-1,5-benzodioxepin-3-ol or an acid addition salt thereof which is free from (S)-(+)-3-[2-(p-hydroxyphenyl)-1-methylethyl]aminomethyl-3,4-dihydro-2H-1,5-benzodioxepin-3-ol in an amount effective to reduce the intraocular pressure.

10. An insert according to claim 9 wherein the acid addition salt is the hydrogen maleate.

11. An insert according to claim 9 wherein the acid addition salt is the dihydrogen phosphate salt.

* * * * *